United States Patent [19]

Maxfield Wilson et al.

[11] Patent Number: 5,776,487
[45] Date of Patent: Jul. 7, 1998

[54] LIPOSOME REAGENTS FOR IMMUNOASSAYS

[75] Inventors: Nancy Maxfield Wilson, Bloomington, Minn.; Catherine Larue, Vaucresson, France

[73] Assignee: Pasteur Sanofi Diagnostics, Marnes la Coquette, France

[21] Appl. No.: 634,969

[22] Filed: Apr. 19, 1996

[51] Int. Cl.$^6$ ...................................................... A61K 9/127
[52] U.S. Cl. .......................... 424/450; 435/7.1; 435/7.9; 435/7.92; 436/501; 436/518; 436/543; 436/829
[58] Field of Search .................... 424/450; 435/7.1, 435/7.9, 7.92; 436/501, 512, 518, 543, 829

[56] References Cited

U.S. PATENT DOCUMENTS

| | | | |
|---|---|---|---|
| 4,193,983 | 3/1980 | Ullman et al. | 436/528 |
| 4,235,871 | 11/1980 | Papahadjopoulos et al. | 424/450 |
| 4,483,929 | 11/1984 | Szoka | 436/533 |
| 4,485,054 | 11/1984 | Mezei et al. | 264/4.6 |
| 4,668,638 | 5/1987 | Janoff et al | 436/506 |
| 4,698,299 | 10/1987 | Janoff et al | 435/13 |
| 4,717,676 | 1/1988 | Wagner et al | 436/501 |
| 4,762,915 | 8/1988 | Kung et al. | 424/19 |
| 4,783,400 | 11/1988 | Canova-Davis et al. | 435/7.9 |
| 4,839,276 | 6/1989 | Adolfsen et al. | 435/7.72 |
| 4,874,710 | 10/1989 | Piran | 436/518 |
| 4,933,121 | 6/1990 | Law et al. | 264/4.3 |
| 4,948,590 | 8/1990 | Hawrot et al. | 424/450 |
| 5,017,501 | 5/1991 | Wong | 436/528 |
| 5,094,785 | 3/1992 | Law et al. | 264/4.3 |
| 5,106,963 | 4/1992 | Hwang et al. | 436/71 |
| 5,108,934 | 4/1992 | Rokugawa et al | 436/512 |
| 5,248,590 | 9/1993 | Rutner et al. | 435/5 |
| 5,296,347 | 3/1994 | LaMotte, III | 435/5 |
| 5,312,730 | 5/1994 | Piran et al. | 435/7.92 |
| 5,344,758 | 9/1994 | Krilis et al. | 435/7.1 |
| 5,374,715 | 12/1994 | Kanno et al. | 530/402 |
| 5,399,331 | 3/1995 | Loughrey et al. | 424/450 |
| 5,494,803 | 2/1996 | Carbonell et al. | 435/7.92 |

FOREIGN PATENT DOCUMENTS

| | | |
|---|---|---|
| 0036277 | 3/1981 | European Pat. Off. . |
| 0245926 | 3/1987 | European Pat. Off. . |
| 2 021 262 A | 4/1979 | United Kingdom . |
| 8501580 | 4/1985 | WIPO . |
| 9110138 | 7/1991 | WIPO . |

OTHER PUBLICATIONS

Bruce P. Gaber, et al., "Liposome-Based Immunoassays for Detection of Small and large Molecules," *Adv. Exp. Med. Bio.*, 238, 209-214 (1988).

Rodney J. Y. Ho, et al., "Interactions of Antigen-Sensitized Liposomes with Immobilized Antibody: A Homogeneous Solid-Phase Immunoliposome Assay," *The Journal of Immunology*, vol. 134, No. 6, Jun. 1985, p. 4035-4040.

Yoshio Ishimori, et al., "Stable Liposomes for Assays of Human Sera," *Clinical Chemistry*, 39/7, 1439-1443 (1993).

Troy D. Jaskowski, et al., "Comparison of Three Commercially Available Enzyme Immunoassays for the Screening of Autoantibodies to Extractable Nuclear Antigens," *Journal of Clinical Laboratory Analysis*, 9:166-172 (1995).

Kari Keinänen, et al., "Biosynthetic Lipid-Tagging of Antibodies," *FEBS Letters*, 346 (1994) 123-126.

Lee D. Lesserman, et al., "Covalent Coupling of Monoclonal Antibodies and Protein A to Liposomes: Specific Interaction with Cells in Vitro and in Vivo," *Liposome Technology*, vol. III Chapt. 2, 29-39 (©1984, 1992).

H.C. Loughrey, et al., "Optimized Procedures for the Coupling of Proteins to Liposomes," *Journal of Immunological Methods*, 132 (1990) 25-35.

H. Patrick McNeil, et al., "Immunology and Clinical Importance of Antiphospholipid Antibodies," *Advances in Immunology*, vol. 49, 193-280 (©1991).

Eng M. Tan, "Antinuclear Antibodies: Diagnostic Markers for Autoimmune Disease and Probes for Cell Biology," *Advances in Immunology*, vol. 44, 93-151 (©1989).

Walter L. Binder, "The Anticardiolipin ELISA Test,"*American Clin. Lab*, Oct. 1992.

Timothy D. Heath, et al., "The Development and Application of Protein-Liposome Conjugation Techniques," *Chemistry and Physics of Lipids*, 40 (1986) 347-358.

Rodney J. Y. Ho, et al., "Target-Sensitive Immunoliposomes: Preparation and Characterization," *Biochemistry*, 1986, 25, 5500-5506.

Kenji Hosoda, et al., "Homogenous Immunoassay for $X_2$ Plasmin Inhibitor ($X_2$PI) and $X_2$ PI-Plasmin Complex. Application of a Sandwich Liposome Immune Lysis Assay (LILA) Technique," *Journal of Immunological Methods*, 121 (1989) 121-128.

Chong-Kook Kim, et al., "Liposome Immunoassay (LIA) with Antigen-Coupled Liposome Containing Alkaline Phosphatase," *Journal of Immunological Methods*, 159 (1993) 101-106.

Laurie Locascio-Brown, et al., "Liposome-Based Flow-Injection Immunoassay for Determining Theophylline in Serum," *Clinical Chemistry*, vol. 39, No. 3, 1993 p. 386-391.

R. A. Schwendener, et al., "n-Alkyl-Glucosides as Detergents for the Preparation of Highly Homogenous Bilayer Liposome of Variable Sizes (60-240nm 0) Applying Defined Rates of Detergent Removal by Dialysis," *Biochemical and Biophysical Research Communications*, vol. 100, No. 3, 1055-1062, 1981.

(List continued on next page.)

*Primary Examiner*—Gollamudi S. Kishore
*Attorney, Agent, or Firm*—Fredrikson & Byron, P.A.

[57] ABSTRACT

The present invention relates to the detection of a variety of analytes in a patient sample employing liposomes with associated ligand, where the ligand is capable of binding target analyte in that sample. In another aspect of the invention, the assays employ liposomes as a soluble support matrix where at least a portion of the support is associated with the ligand and the ligand is in a confirmation permitting it to bind to target analyte in a patient sample.

43 Claims, No Drawings

OTHER PUBLICATIONS

Regan G. Shea, et al., "Synthesis Hybridization Properties and Antiviral Activity of Lipid–Oligodeoxynucleotide Conjugates,"*Nucleic Acids Research*, vol. 18, No. 13, p. 3777–3783 (©1990).

Francis Szoka, Jr., et al., "Comparatice Properties and Methods of Preparation of Lipid Vesicle (Liposomes0," *Ann. Rev. Biophy, Bioeng.,* 1980 9:467–508.

Package Insert for Diastat Anti–Cardiolipin Kit. (Undated).

Package Insert for Diastat Total Anti–Cardiolipin Kit. (Undated).

Shield Diagnostics Ltd., Diastat Anti–Cardiolipin IgG and IgM Kit for in vitro diagnostic use 96 Test Kit. (Undated).

Edwin F. Ullman, et al., "Use of Liposome Encapsulation in a Combined Single–Liquid Reagent for Homogenous Enzyme Immunoassay," *Clinical Chemistry,* 33/9, 1579–1584 (1987).

Mamoru Umeda, et al., "Application of Sandwich Method to Determine a Serum Protein Component with Antibody–Bearing Liposomes,"*Journal of Immunological Methods,* 95 (1986) 15–21.

LIPOSOME REAGENTS FOR IMMUNOASSAYS

FIELD OF THE INVENTION

The present invention relates to immunoassays utilizing novel liposome reagents having ligand associated with or incorporated into the liposome to facilitate the detection of analyte in a patient sample. In one embodiment the invention relates to the detection of a variety of analytes in a patient sample employing liposomes with associated ligand where the ligand is capable of binding target analyte in that sample. In another embodiment of this invention the assay employs liposomes as a soluble matrix support where at least a portion of the support is associated with a ligand and the ligand is in a conformation permitting it to bind to target analyte in a patient sample.

BACKGROUND OF THE INVENTION

This invention details novel assay formats employing novel liposome reagents in assays to detect analyte in a patient sample. In one embodiment of this invention, lipids are formulated into liposomes that incorporate target ligand to detect analyte in a sample. Often the detection of analytes such as those associated with a particular autoimmune disease is difficult because the concentration of analyte in a patient sample is very low. The use of phospholipids to support ligand in a liposome permits increased ligand binding capacity within the assay. In microplate format assays where ligand or analyte is bound directly to the solid phase, molecular interactions may be sterically hindered. In contrast, with the assay format of the present invention, the ligand is intercalated into a more fluid gel-type matrix which can allow substantial steric flexibility. Moreover, assays employing the liposome reagent can have the advantage of presenting ligand for detection or interaction with the analyte in a more native conformation than in solid phase assays where ligands directly bind to the surface and are often structurally altered.

The use of liposomes comprised of phospholipids as reagents in homogeneous immunoassays to detect analytes has been described. These assays employ liposomes to encapsulate reporter molecules. U.S. Pat. No. 5,248,590 to H. Rutner et al. states: "When used in an immunoassay, a liposome generally encapsulates a reporter molecule such as a dye or an enzyme and is complexed with a ligand, usually an antigen or antibody." Examples of these assays are described in U.S. Pat. Nos. 4,193,983 to Ullman, et al., 4,483,929 to Szoka, 4,783,400 to Canova-Davis, et al., 4,874,710 to Piran and 4,668,638 to Janoff, et al. In these assays the liposome may be complexed with ligand either covalently or noncovalently through intercalation with hydrophobic molecules or portions of such molecules into the hydrophobic bilayer. The ligand is usually an antibody or antigen that specifically binds the analyte to be detected in the sample. In the cited examples, when the liposome-associated ligand is contacted with a patient's sample, analyte in the sample complexes with the ligand resulting in lysis of the liposome, typically through a complement-mediated lysis. The amount of reporter molecule released into the aqueous solution is determined and this amount is related to the concentration of the analyte being detected.

Significant problems associated with these reporter-encapsulated immunoassays have been identified. First, liposome based assays which require lysis are susceptible to non-specific lysis either by endogenous complement present in the test sample or by liposome degradation leading to leakage of the reporter molecule from the liposome. Therefore, maintaining the integrity of the liposomes is essential to reporter-encapsulated assay sensitivity and specificity. A second disadvantage of lysis-mediated liposomal detection systems is that when the concentration of a particular analyte in a patient sample is low, the use of a more concentrated test sample can result in non-specific liposome lysis due to the presence of endogenous complement, and the like, unless the test sample is pre-treated to remove such components. Sample pre-treatment, however, adds time and costs to any assay. Moreover, the pre-treating agent must be carefully chosen so that analyte present in the sample is not denatured or degraded by the agent and the integrity of the liposome is not affected.

While maintaining many of the advantages of liposome-based assays currently in use, as described previously, assays of this invention extend the applicability of prior assay designs by overcoming deficiencies limiting the utility of the liposome encapsulated reporter assay approach. For example, the present invention does not rely on encapsulated reporter. Maintaining integrity of the liposomes is not a requirement for functionality with this invention. In addition, significant advantages may be seen over microplate ELISA formats due both to increased binding capacity and steric flexibility.

There are also limitations associated with the detection of analyte in microplate ELISA-type assays. The microplate ELISA-type assays require the physical attachment of the ligand directly to a solid phase. As discussed above, direct coupling may increase the risk of reduced sensitivity in these assays due to the steric hindrance imposed on either ligand, analyte, or both, that may prevent these molecules from reacting efficiently.

In contrast, the present invention provides a means of binding analyte to a solid phase through the use of the liposome reagent which can result in reduction of problems associated with steric hindrance. It can better maximize the efficiency of ligand and analyte recognition, and increase the total ligand binding capacity of the solid phase. This invention combines these features and also provides compositions and methods readily adaptable for a fully automated system.

SUMMARY OF THE INVENTION

The present invention provides methods for determining the presence or amount of analyte in a test sample comprising contacting a liposome reagent, the liposome reagent comprising a liposome, a ligand chosen to bind specifically with the analyte and associated with the liposome membrane, and a haptenated component associated with the membrane of a liposome, and where the hapten is chosen to bind specifically to a receptor on the solid phase of the assay, or to a component of the signal detection system used in the assay, with test samples and the solid phase having the receptor to the hapten immobilized thereon, simultaneously or sequentially for a time and under conditions sufficient for the analyte in the sample to bind to ligand in the liposome reagent and for the liposome reagent to bind to the receptor of the solid phase; and detecting the presence or amount of analyte bound to the solid phase. Preferably this method further comprises the step of determining the amount or presence of analyte by contacting the solid phase to which analyte in the test sample is bound with a predetermined amount of a labeled reagent that will specifically bind to the analyte and detecting the label.

Preferably the label is selected from a group consisting of enzymes, radioisotopes, stable-free radicals, chemiluminescent compounds, bioluminescent compounds, pigments, fluorescent compounds, dyes and enzymes substrates. Preferably the label is an enzyme and the enzyme is selected from the group consisting of alkaline phosphatase and horseradish peroxidase. Preferably the solid phase is selected from the group consisting of microtiterplates, polystyrene beads, magnetic particles, nitrocellulose strips, membranes, latex micro particles, and particles prepared from hydrocarbon polymers including polystyrene and polypropylene, glass, metals and gels. More preferably, the solid phase is a suspendable particle. In a particularly preferred embodiment of this invention the solid phase is a paramagnetic particle.

In yet another aspect of this invention, a liposome reagent is disclosed for use in an assay to detect analyte in a test sample containing analyte comprising a liposome; a ligand chosen to bind specifically to the analyte and associated with the liposome membrane; and a haptenated component associated with the liposome membrane, where the hapten is chosen to bind specifically to either a receptor on a solid phase or to a component of the signal detection system used in the assay; and where the ligand and haptenated component remain associated with a portion of the bilayer to maintain the linkage between the solid phase and ligand. Preferably the ligand comprises a protein, polypeptide or peptide fragment, and preferably the ligand includes an antibody fragment capable of binding proteins.

In one embodiment of this aspect of the invention, the ligand is nucleic acid and in another embodiment of this aspect of the invention, the analyte is antibody present in a patient sample. In one embodiment the ligand is covalently associated with the liposome and in another embodiment the ligand is noncovalently associated with the liposome. In a preferred embodiment the ligand is Ro and also preferably the ligand is La.

This invention also relates to a method for determining the presence or amount of antibodies to an autoimmune determinant in the test sample comprising the steps of: contacting a liposome reagent comprising a liposome, a ligand chosen to bind specifically with the antibodies to the autoimmune determinant associated with the liposome membrane and haptenated component associated with the liposome membrane and where the hapten is chosen to bind specifically to a receptor on a solid phase of the assay, with test sample and the solid phase having the receptor to the hapten immobilized thereon, simultaneously or sequentially for a time and under conditions sufficient for the antibodies to the autoimmune determinant present in the sample to bind to the ligand in the liposome reagent and for the liposome reagent to bind to the receptor on the solid phase; and detecting the presence or amount of antibodies to the autoimmune determinant bound to the solid phase. In one preferred embodiment of this method, the ligand is Ro. In another preferred embodiment of this invention, the ligand is La. Preferably, the haptenated component is a haptenated phospholipid and still more preferably, the phospholipid that is haptenated is selected from the group consisting of cardiolipin, phosphapidylinositol, phosphatidylcholine, phosphatidylserine, phosphatidylethanolamine, sphingomyelin and phosphatidic-acid. In a particularly preferred embodiment of this invention, the haptenated phospholipid is haptenated dipalmitoylphosphatidylethanolamine.

In another embodiment of this invention, a kit is disclosed for use in an assay to determine the presence or amount of analyte present in a test sample comprising a liposome reagent, the liposome reagent comprising a liposome, a ligand chosen to bind specifically to the analyte and associated with the liposome membrane and a haptenated component associated with the liposome membrane, where the hapten is chosen to bind specifically to either a receptor on a solid phase and where the liposome is prepared so that during the assay the ligand and haptenated component remain associated with a portion of the bilayer to maintain a linkage between the solid phase and the ligand. The kit also includes solid phase with receptor and labeled detector for analyte.

In another aspect of this invention, a liposome reagent is disclosed for use in an assay to detect antibodies in a test sample comprising a liposome; a phospholipid ligand chosen to bind specifically to the antibodies and associated with the liposome membrane and a haptenated component associated with the liposome membrane and where the hapten is chosen to bind specifically to a receptor on a solid phase using the assay; and where the liposome is prepared so that during the assay, the ligand and haptenated component remain associated with a portion of the bilayer to maintain a linkage between the solid phase and phospholipid ligand.

This invention also relates to a liposome reagent for use in an assay to detect analyte in a test sample comprising a liposome; a ligand chosen to bind specifically to the analyte and associated with the liposome membrane; a haptenated component associated with the liposome membrane where the hapten is chosen to bind specifically to a receptor on a solid phase; and a label compound that is an element of a signal detection system associated with the liposome membrane. Preferably, the label compound is an enzyme and, in a particular embodiment of this invention, the label compound is alkaline phosphatase.

This invention also relates to a method of determining the presence or amount of an analyte in a test sample comprising the steps of contacting a liposome reagent with test sample and a solid phase having a receptor for analyte bound thereto for a time and under conditions sufficient for the analyte in the sample to bind to ligand in the liposome reagent, the liposome reagent comprising a liposome; a ligand chosen to bind specifically to the analyte and associated with the liposome membrane; and a label compound that is an element of a signal detection system associated with the liposome membrane; and measuring the amount of analyte bound to the solid phase.

In another aspect of this invention, the invention relates to a liposomal soluble support matrix for use in an assay to detect analyte in a test sample comprising; a first liposome reagent comprising a liposome having a ligand chosen to bind specifically to analyte in a test sample, wherein the ligand is associated with the liposome membrane; and a haptenated component associated with the liposome membrane, wherein the hapten is selected to bind specifically to a receptor; and a second liposome reagent comprising a liposome having the receptor wherein during the assay the haptenated component on the first liposome reagent binds the receptor on the second liposome reagent to form the soluble support matrix. Preferably the ligand comprises a protein, polypeptide, or peptide fragment and more preferably the ligand includes antibody fragments capable of binding protein. In a particularly preferred embodiment, the hapten portion of the haptenated component is biotin.

In yet another aspect of this invention, a liposomal soluble support matrix is disclosed for use in an assay to detect analyte in a test sample comprising; a liposome reagent comprising a liposome, a ligand chosen to bind specifically to the analyte and associated with the liposome membrane, a haptenated component associated with the liposome membrane, where the hapten is chosen to bind specifically to a receptor; and wherein during the assay, receptor is added to bind the haptenated component and form the soluble support matrix. Preferably the ligand comprises a protein, polypeptide or peptide and preferably the haptenated component is biotin. In a particular preferred embodiment, the receptor is neutravidin.

This invention also relates to a method for determining the presence or amount of analyte in a test sample using a soluble liposomal support matrix comprising the steps of contacting a ligand bearing haptenated liposome reagent with a test sample, a receptor, and a receptor bearing solid phase simultaneously or sequentially for a time and under conditions sufficient for analytes present in the sample to bind to the ligand in the liposome reagent, for the receptor to bind the liposome reagent to form a matrix and for the liposome reagent to bind to the receptor on the solid phase, said ligand-bearing liposome reagent comprising a liposome, a ligand chosen to bind specifically with analyte in a test sample, and haptenated component associated with the bilayer of the liposome where the hapten is chosen to bind specifically to the receptor and to the receptor bearing solid phase and detecting the presence or amount of analyte bound to liposome reagent bound to the solid phase. Preferably the hapten of the liposome reagent is biotin and the receptor is selected from a group consisting of neutravidin, streptavidin, avidin, or an antibody capable of specifically binding to biotin.

In another aspect of this invention, a method is disclosed for determining the presence or amount of antibodies to an allergen in a test sample comprising contacting a liposome reagent comprising a liposome, a ligand chosen to bind specifically with the antibodies to the allergen and associated with the liposome membrane and haptenated component associated with the bilayer of the liposome and where the hapten is chosen to bind specifically to receptor on a solid phase of the assay, with test sample and the solid phase having the receptor to the hapten immobilized thereon, simultaneously or sequentially for a time and under condition sufficient for the antibodies to the allergen present in the sample to bind to the ligand in the liposome reagent and for the liposome reagent to bind to the receptor on the solid phase and detecting the presence or amount of antibodies to the allergen bound in the solid phase. Preferably the ligand is an allergen.

In another preferred embodiment of this invention, a kit is provided for use in the assay to determine the presence or amount of analyte present in a test sample comprising a plurality of ligand-bearing haptenated liposome reagent capable of binding to analyte present in the test sample, a receptor capable of binding to the hapten on the haptenated liposome reagent, a receptor bearing solid phase, and labeled detector for analyte detection.

DETAILED DESCRIPTION OF THE INVENTION

This disclosure details liposome reagent compositions suitable for supporting ligand that is capable of binding analyte in a diagnostic assay along with methods for using this reagent. The reagent preferably employs phospholipid to form liposomes and includes various molecules intercalated, encapsulated, or associated with the phospholipid bilayer, depending on the intended use. A variety of applications for this assay are contemplated that relate to the use of the lipid reagent as a support or matrix for various analytes in diagnostic assays.

The following definitions are used throughout:

"Anti-phospholipid antibodies" refers to antibodies which generally bind to negatively charged phospholipids, including cardiolipin (diphosphatidylglycerol), phosphatidylserine, phosphatidylinositol and phosphatidic acid.

"Analyte" is used herein to refer to the compound or composition to be measured, preferably from a patient sample. The analyte is preferably one member of a specific binding pair and preferably the other member of the binding pair is ligand. Analytes useful with the assays of this invention include proteins, including antibodies, antigens, nucleic acids, steroids, hormones and the like, having specific binding affinity for either ligand or an analyte receptor to which ligand binds.

"Ligand" is used herein to refer to a compound, molecule or the portion of the molecule that is a member of a specific binding pair, the other member of which is either analyte or a receptor to which analyte binds. Ligand is chosen to specifically bind to analyte or analyte receptor so that the amount of analyte bound to the ligand or analyte receptor during an assay is related to the amount of analyte present in the test sample. Ligand also includes ligand analogs where the ligand molecule is modified such that the portion of the molecule that specifically binds analyte or a receptor for analyte is removed from the native molecule either through chemical, enzymatic or molecular manipulations and is affixed or associated with another molecule. Ligands are generally the smaller of the two components of the specific binding pair; however, this is not necessarily so. The ligand has one or more epitopes, may be antigenic or haptenated, and may be one or a group of compositions sharing at least one epitopic site. Illustrative ligands include autoantigens, allergens, anionic phospholipids, antibodies to tumor markers, and the like. The ligands of this invention are said to be "associated with" the liposomes of this invention. The term "associated with" is used herein to describe a stable interaction between the ligands of this invention and the liposomes of this invention by either covalent or non-covalent means.

"Hapten" or "Haptenated" is used herein to refer to one member of a specific binding pair alone or attached to another compound or molecule where the other member is a receptor that is not analyte or ligand. Haptens are generally low molecular weight compounds capable of eliciting immune responses in laboratory animals, usually when conjugated to a carrier. Examples of haptens include biotin, dinitrophenyl groups (DNP), fluorescein or its derivatives, such as fluorescein isothiocyanate (FITC), digoxigenin, and the like. The term "haptenated component associated with the membrane of the liposome" refers to a stable interaction between the haptenated components of this invention and the liposomes of this invention by either covalent or non-covalent means.

"Receptor" is used herein to refer to any compound or composition having specific binding for a hapten or haptenated compounds, ligand or analyte. Receptors useful with assays of the invention include antibodies, such as anti-biotin and anti-digoxigenin antibodies, anti-analyte antibodies and other binding substances such as avidin, streptavidin, lectins, enzymes, intrinsic factor, folate binding protein, and the like.

"Label" or "labeled" is used herein to refer to a compound which is either directly or indirectly involved with the production of a detectable signal as part of a signal detection system and is bonded directly to one or more molecules of a component of the assay in an amount related to the amount of analyte in the sample. Label may be conjugated to carriers that specifically bind to analyte or ligand or may be incorporated into or associated with the membrane of a liposome reagent. Illustrative examples of labels include any of those known in the art, including enzymes, fluorophores, radioisotopes, stable free radicals, luminescers, such as chemiluminescers, bioluminescers and the like, dyes, pigments, enzyme substrates and other labels known in the art. The term "detector" refers to any compound associated with a label. In a preferred signal detection system, the label is an enzyme and the detectable signal may be generated by exposing the labeled reagent to a particular substrate and incubating for color, fluorescence or luminescence development.

"Liposome" is used herein to refer to small discrete particles capable of maintaining their basic structural integrity in an aqueous environment. The liposome is formed from amphipathic molecules which have their hydrophilic surfaces exposed to surrounding aqueous medium, as well as hydrophilic surfaces exposed to an inner aqueous space. The membrane of the liposome shall be referred to as "membrane bilayer", "bilayer" or "membrane" interchangeably and the membrane forms a transitional zone between two aqueous environments. Liposomes, as used in this invention, include MLVs (MultiLamellar Vesicles), which are comprised of multiple layers of lipid.

"Kit" is used herein to refer to a combination of reagents usually formulated with necessary buffers, salts, and stabilizers, where the reagents are premeasured so as to at least substantially optimize the assay sensitivity.

The term "protein" is used herein to include molecules with protein components, polypeptide and peptide fragments greater than or equal to ten amino acids in length.

The term "allergen" is used herein to refer to any substance that causes manifestations of allergy. It may or may not be a protein. Among common allergens are inhalants such as dusts, pet dander, pollens, fungi, smoke particulate, perfumes; foods including wheat, eggs, milk, chocolate, seafood and the like; drugs including aspirin, antibiotics, serums, and a wide range of chemical compounds; infectious agents including bacteria, viruses, fungi, animal parasites; contactants including chemicals, animals, plants, metals; and the like.

The term "simultaneously" means that the components of the assay such as the liposome reagent, test sample or solid phase with immobilized receptor are each added to a reaction vessel at the same time or one immediately after the other so that all components are combined in a reaction mixture.

The term "sequentially" as used here means that one component of the assay such as the liposome reagent is contacted with another component of the assay such as the test sample and/or solid phase for a time sufficient for a reaction to occur before other components are added to the reaction mixture.

In a first embodiment of this invention, ligands are associated with liposomes to form a liposome reagent. The liposomes are prepared as a mixture of phospholipid or modified phospholipid, haptenated moiety and ligand, including one or more inert or negatively charged phospholipids. Preferably, the phospholipid is cardiolipin and still more preferably the cardiolipin is combined with other phospholipids to create the liposome reagent. Other phospholipids that could be used in this invention include, but are not limited to phosphatidylserine, phosphatidylinositol, phosphatidylethanolamine (used in combination with other phospholipids), phosphatidylcholine, phosphatidic acid, sphingomyelin and the like. These lipids in various combinations form the liposomes of this invention.

In addition to the lipid forming the liposome and a ligand, the liposomes of this invention also include haptenated moieties such as a haptenated lipid or a haptenated protein. In a preferred embodiment of this invention the haptenated moiety is a haptenated phospholipid and still more preferably, the haptenated phospholipid is biotinylated dipalmitoylphosphatidyl ethanolamine (DPPE). Haptenated phospholipids refer to lipids suitable for forming liposomes that have hapten attached in the hydrophilic portion. These haptenated lipids include lipids covalently linked to biotin, avidin, fluorescein or its derivatives such as fluorescein isothiocyanate (FITC) digoxigenin, or the like. The hapten is desirably a low molecular weight compound, such as biotin, that can be readily attached to a lipid. Haptenated phospholipids useful with this invention can be purchased commercially, such as biotinylated dipalmitoylphosphatidyl ethanolamine (DPPE) available from Pierce Chemicals, Rockford, Ill., or the haptenated lipids can be manufactured using the methods disclosed by Rivnay, et al. (see "Use of Avidin-Biotin Technology for Liposome Targeting," in *Methods in Enzymology*, Vol. 149, pgs. 119–123, 1987).

Briefly, the phospholipid is dissolved in a solution of chloroform-methanol containing biotinyl N-hydroxysuccinimide ester (BNHS), followed by the addition of a chloroform solution containing 15% (v/v) triethylamine. The reaction proceeds for about two hours at room temperature and then the mixture is stored at about −70° C. Purification is performed using gradient high-performance liquid chromatography. The column is first washed with a solvent mixture containing n-hexane/2-propanol/water (60:80:14, v/v/v) until a steady baseline is established followed by the introduction of a different solvent mixture containing n-hexane/2-propanol/water (60:80:7, v/v/v) until a new baseline of about 0.07 optical density (OD) units above the first baseline is established. Then the lipid sample is applied and the elution monitored with a M-441 discrete-wavelength ultraviolet detector (214 nm). The column is then eluted with the solvent solutions described above, 5 minutes with the second solution followed by a 20-minute linear gradient between 0 and 100% of the first solvent solution in the second. Then further elution in the first solvent for 45–70 minutes is performed to achieve a stable baseline. The peaks are collected, the eluted material pooled, and the solvent evaporated under a stream of nitrogen.

In a preferred embodiment of this invention, the unmodified negatively charged phospholipids include cardiolipin and the haptenated phospholipids include biotinylated DPPE. Other contemplated combinations include phosphatidylserine with biotinylated DPPE or phosphatidylinositol with biotinylated DPPE. However, any of a variety of lipid combinations, including combinations of anionic phospholipids, with neutral or zwitterionic phospholipids are also contemplated.

Ligand can be obtained from a variety of sources and is selected based on its ability to bind to analyte in a patient sample. Thus, the ligands include antigen, that is, any molecule or compound capable of binding to antibody in a patient sample or the ligand may comprise antibody capable of recognizing antigen in a patient sample. The ligand may include protein, protein fragments, nucleic acid, or other molecules capable of binding to analyte in a patient sample where the presence of analyte is indicative of a medical condition, the presence of disease, infection, or is prognostic of a particular medical outcome. In addition, the ligand may include steroids and the like which do not bind analyte but bind competitively with analyte to a receptor for analyte and are used to measure or to detect analyte in the sample.

Once the appropriate ligand is associated with the liposome bilayer and with a haptenated moiety, the liposome reagent can be used to detect analyte. Analyte present in a patient sample binds to the ligand associated with the liposome and is captured by a solid phase via the haptenated lipid. In a preferred embodiment of the invention, magnetically attractable particles conjugated to anti-biotin antibodies are used to capture biotinylated phospholipid associated with the target ligand.

While a preferred embodiment of this invention relates to the diagnosis of autoantibodies through the association of autoantigens with liposomes, a variety of ligands can be associated with the liposomes of this invention to form liposome reagent suitable for use in diagnostic assays. In a particularly preferred embodiment the reagent is prepared with ligand capable of binding analyte in a patient sample where the presence of antibodies is associated with autoimmune disease. Exemplary antibodies associated with autoimmune diseases include antinuclear antibodies that recognize determinants on the ribonucleoproteins Ro, La, Sm (Smith antigen) or RNP (ribonucleoprotein).

The Sm antigen-antibody system was characterized in patients with SLE and mixed connective tissue disease. Steitz and colleagues (Lerner, et al. *Proc. Natl. Acad. Sci. (USA)* 76:5495–5497, 1979) demonstrated that Sm antibody immunoprecipitated small ribonucleoprotein particles resident in the nucleus and that the particles consisted of a class of small nuclear RNA's called U RNAs which were complexed with several nuclear proteins. The clinical designation Sm refers to proteins with molecular weights of 29, 28, 16 and 13 kilodaltons complexed with U1, U2 and U4–U6 snRNA spliceosome components (see Tan, E. M. *Adv. in Immunol.* 44:93–151, 1989).

The ribonucleoprotein (RNP) antigen-antibody system was characterized in patients with systemic lupus erythematosus (SLE) and mixed connective tissue disease (MCTD). The ribonucleoprotein particles have been shown to be involved in splicing of mRNA. Antibody to nuclear RNP binds to proteins with molecular weights of 70, 33, and 22 kilodaltons complexed with U1 snRNA spliceosome component.

In both cases where antibody is directed to either Sm or ribonucleoprotein, the antigenic determinants are found in the protein component and not the RNA component. In contrast to nuclear RNP, ribosomal RNP corresponds to phosphoproteins having 38, 16 and 15 kilodaltons molecular weight associated with ribosomes.

Autoantibodies directed against SS-A or Ro and SS-B or La were identified in patients with Sjögren's syndrome and SLE. Ro and La autoantibodies have been shown to target intracellular proteins which may be involved with regulation of RNA polymerase III function. Ro corresponds to proteins of 60 and 52 kilodaltons complexed with Y1 to Y5 RNA. La antigen corresponds to a phosphoprotein of 48 kilodaltons complexed with nascent RNA polymerase III transcripts.

The Ro antigen was first isolated from extracts of human spleen in an immunodiffusion precipitation reaction with antibodies in sera from SLE patients. The La antigen was also identified in human spleen extracts with SLE sera. The origin of both antigens is nuclear. La is capable of interacting with a number of small RNA species. It has also been reported that the antigen binds to U1 RNA and to vesicular stomatitis virus leader RNA.

While a preferred embodiment of this invention relates to the diagnosis of autoantibodies through the direct association of the aforementioned antigens into liposomes, it will be understood by those skilled in the art that it is possible to associate a variety of ligands with liposomes either through covalent or noncovalent associations to identify a variety of clinical or pre-clinical conditions.

The liposome reagents of this invention may be formed by a variety of methods known in the art. For example, the present methods employ a modification of the methods described by Szoka, et al. (*Ann. Rev. Biophys. Bioeng.* 9:467–508, 1980) and Plant et al. (*Analyt. Biochem.* 176: 420–426 (1989), the teachings of which are incorporated herein by reference. A preferred method for forming liposomes, as further shown in Example 1 of this specification, is a modification of the method described by D. Papahadjopoulos and F. Szoka, Jr., in U.S. Pat. No. 4,235,871. Briefly, this process comprises three steps: (a) preparation and mixing of a solution of lipid to be deposited in an organic solvent; (b) evaporation of the solution to dryness using a solid stream of nitrogen gas to produce a thin film of phospholipid on a glass vessel; and, (c) hydration and formation of liposomes by vortexing (or other mechanical means) in an appropriate buffer. The resulting structure of the membrane bilayer is such that the hydrophobic (non-polar) tails of the lipid orient inward while the hydrophilic (polar) heads orient toward the aqueous phase present both outside and within the encapsulated space. The liposome preparation may be further separated, as needed, by column chromatography as described in Loughrey, et al. (*J. Immun. Meth.*, 132:25–35, 1990), centrifugation and/or dialysis.

Whether a particular protein, polypeptide, peptide, nucleic acid, steroid or other molecule will be associated covalently or noncovalently with the liposome will depend on the chemical nature of that particular molecule. For example, it is possible to prepare liposomes with Ro and La using the methods disclosed in Example 4. Both Ro and La were noncovalently associated with the liposomes. To determine whether a protein can function as a ligand in association with liposomes, the protein is mixed with lipid at various molar ratios, as described in Example 4. Here, liposome reagents were prepared as described in Example 2 except that preparations were hydrated with buffer containing 10 to 100 µg of the ligand to be associated with the liposome.

In certain instances, the ligand will not associate with liposomes in a form that permits detection of analyte in a patient sample or will not incorporate efficiently into the liposome. In these cases phospholipid can be covalently modified to attach ligands including protein, protein fragments, polypeptide, peptides, nucleic acids and the like to the phospholipid moiety. Methods to covalently couple protein and the like to phospholipid are known in the art and include for example those methods disclosed by Martin, et al. (*J. Biol. Chem.* 257:286, 1982) and Ishimori, Y, et al. *J. Immunol. Methods* 75:351, 1984).

Other methods which may be used for liposome formation include those of Batzri and Korn (*BioChim. BioPhys. Acta,* 281:1015, 1973). Methods for producing liposomes with improved stability include the method described by Law, et al., in U.S. Pat. No. 5,094,785 to produce non-aggregating ligand-linked liposomes. Methods for producing liposomes having a consistent liposome size to improve the reproducibility of assay results and manufacturing are described in U.S. Pat. No. 5,017,501.

It is further contemplated that a variety of phospholipid-derived liposomes could be used in the practice of the diagnostic methods of this invention. For example, any of a variety of liposomal structures could be used including unilamellar (possessing a single membrane bilayer) or multilamellar (characterized by multiple membrane bilayers) structures.

It is possible to use the liposome reagent of this invention in an assay as a screen for the detection of autoantibody species. Here, liposomes are prepared with negatively charged phospholipids such as cardiolipin, and the like and further incorporating a variety of ligands capable of binding autoantibodies including Ro, La, and Sm. Other ligand determinants contemplated for use alone or in combination for use as with a screen include RNP, Scl-70 (Scleroderma-70), (histidyl-tRNA synthetase), and other ligands recognized by autoantibodies including DNA, and the like. Where the diagnosis of anti-phospholipid antibodies is not desired, the liposomes can be prepared from inert phospholipids including phospholipids prepared from equal molar ratios of sphingomyelin and cholesterol as described by Wong (U.S. Pat. No. 5,017,501), or dipalmitoylphosphatidylcholine (DPPC), cholesterol, dipalmitoylphosphatidylglycerol (DPPG) liposomes as described by Law, et al. (U.S. Pat. No. 4,933,121), and the like.

Liposome reagents useful as a tool for autoantibody screening can be prepared with a single ligand species associated with liposomes using the methods disclosed in Example 4 and two or more solutions of liposome reagents each having a different ligand species can be mixed to form a screening mixture of liposome reagent. Alternatively, mixtures of two or more ligands can be added to a liposome film preparation, again using the methods of Example 4 or using other methods known in the art to form liposome reagents having a mixture of different ligands associated with the liposome membrane. These liposome reagents can be used for screening purposes in diagnostic assays to detect the presence of any of a variety of analytes. Positive signals in the assay indicate the presence of autoantibodies in the sample and can indicate the presence of an autoimmune disease or of a predisposition to autoimmune disease.

Liposomes can also be associated with nucleic acid for use as liposome reagents in diagnostic assays to screen for antibodies to nucleic acids. Antinuclear antibody testing is most often performed using indirect immunofluorescence or ELISA microplate screening assays. For example, antinuclear antibody associated with collagen based diseases is currently identified using ELISA microplate screens. Indirect immunofluorescence assays are labor-intensive, subjective and adversely affected by variability in the immunofluorescent assay reagents. The use of a liposome reagent assay to detect antibody to nucleic acids has all of the benefits of liposome-based assays over microplate methods as have been discussed throughout this text. It is possible to covalently link nucleic acid fragments to lipids and these liposomes can be used in assays similar to those described in Examples 2 and 4 to detect antibodies to nucleic acid in a patient sample (for example, see Shea, et al. *Nucl. Acid Res.* 18:3777–3783, 1990, describing methods for preparing phospholipid oligonucleotide molecules).

In one embodiment of the assay of the invention, the liposome reagent incorporating a ligand, such as Ro or La and a haptenated moiety such as biotinylated DPPE is used in a heterogeneous assay having a solid phase that includes immobilized receptor for the hapten. Sample suspected of containing analyte is contacted with the liposome reagent and solid phase for a time and under suitable conditions for analyte present in the sample to complex to ligand associated with the liposome membrane and for the liposome reagent-analyte complex to bind to the solid phase through the hapten/receptor interaction. The solid phase with bound analyte is then separated from the sample, washed and then contacted with a labeled receptor for the analyte for a time and under conditions suitable to allow the labeled receptor to bind to the bound analyte. The amount of bound label is then measured and the amount of bound label is related to the amount of analyte that was present in the sample. Generally, the amount of label detected in the sample is related to the amount of analyte in the sample by comparing the signal obtained when samples containing analyte at a known concentration with the signal obtained with the patient sample.

In another embodiment of the invention, the liposome reagent may be complexed with the solid phase to which receptor is bound through the hapten/receptor interaction before the solid phase is contacted with sample. In a preferred assay format, the assay employs magnetically attractable particles to bind the liposome reagent via a haptenated linkage such as liposome-associated biotinylated phospholipid, preferably biotinylated DPPE.

In yet another embodiment the liposome reagent may be used to identify or label analyte which is itself bound to the solid phase via a specific binding site different than the ligand binding site, preferably at a site sufficiently physically separated from the ligand binding site to minimize steric hindrance. In one embodiment, Ro is the ligand and the analyte being detected is anti-Ro antibodies. Anti-human antibodies (capable of binding to the Fc portion of the anti-Ro antibodies) are immobilized on the solid phase. Patient samples suspected of containing anti-Ro antibodies are contacted with the solid phase simultaneously or sequentially with the liposome reagent for a time and under conditions suitable to allow antibodies present in the sample to bind to the solid phase and the liposome reagent. After the bound liposome reagent is separated from unbound materials in the sample, a solution containing a predetermined amount of labeled receptor for the hapten is contacted with the solid phase and after washing to remove unbound material, the amount of bound labeled receptor is determined. This amount is related to the amount of analyte in the sample.

In yet another embodiment of the assay of this invention, the liposome reagent further comprises a label compound, such as an enzyme, and preferably alkaline phosphatase, wherein the label compound is incorporated into or associated with the liposome membrane. In this embodiment, the liposome reagent is mixed with test sample suspected of containing analyte simultaneously or sequentially with a solid phase bearing hapten receptor. As above, after the analyte binds to the ligand of the liposome reagent which in turn is bound to the solid phase via the hapten/hapten receptor interaction, the bound analyte is separated from the unbound materials in the sample and the amount of label detected.

In yet another embodiment of the assay of the invention, small molecules such as steroids and the like (i.e., vitamin B12, ferritin, etc.) can be the ligand associated with the liposome membrane of the liposome reagent for use in a competitive assay format. Typically, in competitive assays an analyte derivative (such as a label-steroid molecule conjugate) is combined with the test sample suspected of containing analyte and with a solid phase carrying a receptor capable of binding both analyte and analyte derivative. Direct labeling of small molecules such as steroid molecules with an enzyme or other protein label can interfere with the ability of the labeled steroid molecule (analyte derivative) to bind to the analyte receptor competitively with analyte.

In this embodiment of the invention, an analyte derivative can be formed comprising a liposome reagent comprising a liposome, a ligand chosen to bind to a receptor competitively with the analyte (i.e. a steroid molecule) associated with the liposome membrane and a haptenated component associated with the liposome membrane. In the assay, the liposome reagent is combined with the test sample and with a solid phase carrying a receptor to which the analyte in the sample binds competitively with the ligand of the liposome reagent, for a time and under conditions suitable to allow the analyte or liposome reagent to bind to the receptor on the solid phase. Then the unbound materials are separated and washed from the bound materials and a predetermined amount of a labeled-antihapten conjugate is combined with the solid phase and the amount of bound liposome reagent determined. The amount of analyte that was present in the test sample can be determined by comparing the amount of liposome reagent bound to the solid phase in a control sample having no "free analyte" with the amount of liposome reagent bound with the test sample. Alternatively, the liposome reagent could comprise a label compound that is an element of a signal detection system associated with the liposomes membrane in place of the haptenated moiety. The decrease in the amount of liposome reagent bound (decrease in signal generation) will be related to the amount of analyte in the test sample. In yet another embodiment of a competitive assay, the solid phase could carry the receptor for the hapten and the receptor to which the analyte and liposome reagent competitively bind could be conjugated to a label compound.

Solid phases useful with the invention are well known in the art and the term "solid phase" refers to an insoluble material to which one component of the assay may be bound. The term "solid phase" can include the walls of test tubes or wells of a microtiter plate, polystyrene beads, magnetically attractable particles (e.g. paramagnetic particles), nitrocellulose strips, membranes, latex microparticles, and others and may be made of hydrocarbon polymers such as polystyrene and polypropylene, glass, metals, gels or other materials. The "solid phase" is not critical and can be selected by one skilled in the art. Desirably, the solid phase is a particulate solid phase having particles that are capable of being suspended during the reaction. The benefits of using particles as the solid phase to facilitate separation are well known and some of the benefits are set forth in U.S. Pat. No. 4,554,088. Preferably, the solid phase particles used in an assay of this invention are magnetically attractable particles such as those described in U.S. Pat. No. 4,554,088. This patent also describes the benefits provided by the use of magnetically attractable particles as the solid phase in assays. Magnetically attractable particles allow the separation step to be done through magnetic separation and thus avoids the necessity of centrifuging or waiting for the particles to settle out of solution.

In the context of this invention, the terms "bound to" or "immobilized" encompass all mechanisms for binding antibodies and proteins, such as the receptor of the hapten/receptor pair of the invention, directly or indirectly to the solid phase so that during the performance of the assay the antibody or protein remains associated with the solid phase. Such mechanisms include covalent binding, non-covalent binding, chemical coupling, absorption by hydrophobic/hydrophobic, electrostatic hydrophilic/hydrophilic or ionic interactions and the like. In a preferred embodiment, the hapten receptor comprises goat antibiotin antibodies indirectly bound to the solid phase by burro anti-goat antibodies absorbed onto the solid phase.

Certain ratios of phospholipid to haptenated phospholipid may function better than others in diagnostic immunoassays. Methods of determining the optimal ratios are known in the art. Where biotinylated DPPE and Cardiolipin are used, molar ratios of 1:2.5 to 1:100 (biotinylated DPPE:Cardiolipin) are contemplated. In a preferred embodiment employing cardiolipin containing liposomes, molar ratios of 1:5 to 1:20 were used and particularly preferred molar ratios of 1:5 to 1:10 were used. Example 3 is provided to demonstrate that a variety of ratios of target ligand to haptenated phospholipid will function in this invention. This example also provides a testing regime useful to optimize a particular assay by identifying optimal lipid ratios. While these assays are directed toward the combination of cardiolipin and biotinylated DPPE, those skilled in the art of lipid chemistry will readily recognize that other ratios of other lipids could similarly be tested for optimal activity without undue experimentation. Moreover, a variety of ligand:phospholipid ratios were also tested in Examples 3 and 4. Therefore, optimal phospholipid ratios should also be maximized with optimal ligand to phospholipid ratios. One skilled in the art will appreciate that Example 4 provides guidance as an exemplary assay for optimizing ratios of ligand and phospholipid.

Once the ligand-containing liposomes have been prepared, it is useful to test the liposomes to ensure that the ligand is specific for the test analyte. Ligand specificity for test analyte can be determined in a number of ways. Example 3 of this specification, details one method for confirming the specificity of the liposomal ligand for the test analyte. As shown in Example 3, various liposome preparations may be prepared using increasing concentrations of ligand. While cardiolipin is used in this example, various concentrations of protein ligand were employed in Example 4. Those skilled in the art will appreciate that the mixed liposomes of Example 4, i.e., liposomes containing phospholipids in combination with other molecules such as protein, steroids, nucleic acids, and the like, can be tested using the regime disclosed in Example 3.

In these assays, test sera known to contain analyte reactive with ligand associated with the liposomes is tested with each liposome preparation. The amount of reactivity is then plotted as a function of ligand concentration employed in the liposome preparation. A linearity of dose with increasing amounts of ligand is used to assess ligand specificity.

Alternatively, competitive assays can be used to demonstrate specificity of ligand binding. In such an assay a sample known to contain anti-ligand antibodies is contacted with unhaptenated ligand incorporated or ligand-associated liposomes and haptenated ligand-incorporated or ligand-associated liposomes. If the ligand is specifically binding with the analyte, the unhaptenated and haptenated liposomes will compete for binding to the same site on the analyte resulting in a reduction of signal detected when the amount of bound analyte is quantitated.

The assays of this invention can be used in either a manual or automated assay format. In the examples, an automated analyzer generally as described in PCT Application No. PCT/US93/04209, published as International Publication No. WO (3/22686) was used. Such an analyzer is commercially available from Sanofi Diagnostics Pasteur, Inc. USA under the trademark ACCESS. Any operation details not set forth below can be readily ascertained from this commercially available analyzer and/or its associated manuals.

There are significant benefits to using the liposome reagents to detect analyte present in serum or test samples at low concentrations. For example, since the liposome has multiple binding sites there is increased capacity to recognize analyte within the assay.

Additionally, the liposome reagents of this invention are more likely to present native ligand structure than are current microplate formats or directly labeled analytes, such as are used in the case of small molecules such as steroids. Further, the epitopes would likely be more accessible to the antibody resulting in enhanced assay sensitivity as compared with assays where the ligand is locked into a particular conformation such as would be found in solid phase assays.

Instability of liposome preparations over time can be a problem with previously described liposome-based assay formats. An advantage of this format is its improved stability. We have found that the liposomes of this invention remain functional for use in assays of this invention when stored under nitrogen at 4° C. for greater than sixteen months, making these preparations particularly suitable for use in assay kits.

In another aspect of this embodiment, it is contemplated that the assays could incorporate allergens into the liposomes. This invention envisions that automated allergy screens could be prepared for any number of allergens including, but not limited to food allergens including seafood, milk, eggs or egg whites and other allergens including molds, pet dander, pollens, dusts, mites and the like. In these assays, the ligand is bound by immunoglobulins present in the patient sample. IgE in patient samples is readily detected through the use of anti-human IgE alkaline phosphatase conjugates such as goat, burro, or mouse anti-IgE conjugates available from a variety of suppliers.

In another embodiment of this invention, ligand is associated with the liposome bilayers and the liposomes form a soluble matrix support by non-covalent cross-linking of haptenated molecules associated with the liposome bilayer via hapten receptors present in the reaction mixture either as free molecules or molecules associated with the liposome bilayers of the liposomes. In one aspect of this embodiment, hapten receptor molecules, such as anti-biotin antibodies, are incorporated into or associated with the liposome bilayer of liposome reagents comprising ligand and a haptenated moiety such as biotinylated phospholipids. These liposome reagents form into a matrix in solution through the biotin/anti-biotin interactions. The soluble liposome support matrix can be formed either during or before contacting it with patient sample. In the example, the receptor itself is multivalent (i.e., able to bind more than one hapten molecule per hapten receptor molecule); however, in another embodiment, the liposome has more than one hapten receptor associated with it and available for hapten binding. In this embodiment, by effectively cross-linking the liposomes having ligand associated with the liposome bilayers, even greater binding capacity is achieved than in the assay format where the individual liposome reagents are bound to a solid phase, without modifying the solid phase to increase liposome reagent binding, an advantage in some systems.

Matrices have been shown to facilitate analyte detection. For example, European Patent Application 0 245 926 to El Shami discloses assays where an immunocomplex is formed between test analyte in a patient sample and corresponding antibody. After the immunocomplex is formed, the complex is immobilized onto a liquid soluble support using an antibody recognizing the corresponding antibody. Unlike the present invention, the liquid soluble supports disclosed by El Shami include dextran and amino acid copolymers.

There are several advantages of a soluble matrix support in a diagnostic assay. For example, as described in European Patent Application 0 245 926, the use of a liquid soluble matrix increases the potential number of immunocomplexes that can be immobilized on a solid support. In addition, the use of a soluble matrix facilitates soluble kinetic interactions between ligand and analyte in contrast to assays having immobilized ligand associated directly with a solid phase.

In contrast to European Patent Application 0 245 926, the present invention employs liposomes to form the soluble matrix. In a preferred embodiment of this invention the matrix comprises liposomes associated with ligand and having a haptenated component associated with the liposome membrane and liposomes having a receptor capable of binding the hapten. In this embodiment there are at least two different liposome populations: one matrix species and one ligand species. For example, one population comprises a receptor capable of binding the haptenated component and another population of liposome comprises the haptenated component and the ligand together on the liposome. In another aspect of the invention there is a single liposome population having the ligand and the haptenated component and a receptor is added that is capable of binding the haptenated component to form a matrix of ligand bearing liposomes.

In another embodiment, ligand-containing haptenated liposomes are associated with non-liposome, anti-hapten receptor at limiting receptor concentrations such that the complex has sufficient hapten available to be captured by the solid phase. As discussed in relation to the other embodiments of this invention, the use of liposomes to support ligand can enhance the stability of the ligand and promote the native conformation of the ligand in solution.

The liposomes used for the soluble matrix support embodiment can be prepared using the methods provided in Examples 1–3, discussed above. Liposomes containing haptenated components and protein ligand are disclosed in Example 4. Liposomes containing the receptor can also be prepared using the methods of Example 4 and the above discussion relating to the incorporation of protein ligand into liposomes.

Other liposome conformations contemplated in this invention for use in matrix-assay formats include haptenated liposomes containing antibodies capable of recognizing analyte in a sample. A variety of methods for associating ligand with liposomes are known in the art. For example, Loughrey, et al. describe optimized procedures for coupling proteins to liposomes (*J. Imm. Methods*, 132:25–35, 1990) and Heath, et al. describe the development and application of protein-liposome conjugation techniques (See *Chemistry and Physics of Lipids*, 40:347–358, 1986).

To prepare a liposome reagent incorporating ligand, the ligand is chosen such that it binds specifically to an analyte in a test sample. Preferably, this liposome reagent also includes a haptenated component also intercalated or associated into the liposome. The hapten is selected to bind specifically to a receptor and the receptor is multivalent. In a particularly preferred embodiment, the haptenated component is a haptenated phospholipid, such as biotinylated DPPE, and the receptor is neutravidin. Liposome reagents prepared containing both the haptenated component and the ligand.

Liposome reagents are mixed with a test sample, including patient sample, and receptor. The receptor is added at a sufficient concentration to form a matrix through its association with the haptenated component of the liposome reagent. In a preferred embodiment, employing a solid phase, the ratios of liposome reagent to receptor are modulated when the assay is optimized so that there is sufficient haptenated component to facilitate capture by a solid phase.

Preferably, solid phase capable of binding to liposome reagent is added to the mixture of liposome reagent, receptor and test sample. The solid phase is used to capture the matrix and matrix formation can be facilitated by a preincubation step. Following an incubation period, the solid phase with bound analyte is separated from the sample, washed and contacted with a labeled specific binder for the analyte for a time and under conditions suitable to allow the labeled binder to bind to the bound analyte. The amount of bound label is then measured and this amount is related to the amount of analyte that was present in the sample. As has been described above, the amount of label detected in a sample is related to the amount of analyte in the sample by comparing the signal obtained when samples containing known concentrations of analyte are compared to the signal obtained with the patient sample.

In a preferred example, liposomes with biotinylated DPPE and ligand were combined with free neutravidin. Ligand containing biotinylated DPPE/cardiolipin liposomes were functionally cross-linked via neutravidin to form the matrix. The ability of the matrix format to detect test analyte in a patient sample was demonstrated using patient serum samples containing antibody to phospholipid and was also demonstrated using samples containing antibody to the ligand. In one method, liposome films containing ligand, phospholipid and neutravidin were rehydrated to form the matrix. In another method, liposome films containing liposome and ligand are rehydrated and neutravidin is added following liposome formation. In a preferred embodiment, the serum samples and liposomes were combined with the matrices and anti-hapten antibodies to magnetic particles. The reaction mixtures were mixed and incubated for 30 minutes at 37° C. before washing. The reaction mixture was incubated with a labeled antibody (for example a monoclonal anti-human Fc-ALP antibody) and the solid phase with bound reagents were separated from the unbound materials, washed, substrate added and signal detected as described above.

References discussed herein are hereby expressly incorporated by reference into this text. Particular embodiments of this invention will be discussed in detail below and reference has been made to possible variations within the scope of the invention throughout this document. There are a variety of alternative techniques and procedures available to those of skill in the art which would similarly permit one to successfully practice the claimed invention without undue experimentation.

EXAMPLE 1

Preparation of Liposomes

In this example, liposomes were prepared using a mixture of the phospholipids, cardiolipin (also the ligand in these examples) and biotinylated dipalmitoylphosphatidylethanolamine (bt-DPPE, Pierce Chemicals, Rockford, Ill.).

To prepare a stock preparation of liposomes, a 0.2 ml–0.5 ml volume of ethanol containing 1 µmole (total) of phospholipid at a molar ratio approximately 1:20 bt-DPPE:CL (mixed by vortexing) was dried onto 12×75 mm glass tubes under a stream of nitrogen or argon gas, preferably for one half hour beyond evaporation of visible solvent. If the total phospholipid solution was not sufficient to cover the bottom of the tube (less than or equal to 0.3 ml), additional ethanol was added before drying. Tubes having dried phospholipid film were stored in a dessicator under argon or nitrogen or under vacuum at ambient temperature for periods of up to several weeks until the films were hydrated to form liposomes. Lipid films stored under these conditions showed no observable decrease in the functionality of the liposome reagents.

To prepare liposomes, the lipid films prepared as above were hydrated by adding phosphate buffered saline (PBS, pH 7.2–7.4) to an appropriate hydration volume, and vortexing vigorously for about a minute. Other buffers used in this hydration step include Tris-buffered saline (TBS, pH 7.4) and PBS with 1% protein, either bovine serum albumin (BSA) or human serum albumin (HSA). When the phospholipid concentration in the hydration solution was sufficiently high (e.g., 1 mg/ml from input lipid solids) and the solution was visibly cloudy the samples were vortexed. After vortexing the liposome preparation, it was incubated for 30–60 minutes by shaking in an orbital type shaker to increase liposome yield. This step can also produce more uniformly sized liposomes in the preparation.

Unincorporated molecules were separated from the liposome preparations using three methods. In these examples, the liposome preparations were micro-centrifuged at approximately 13,000×g, washed with PBS and the pellet fraction was isolated for use.

Another method of separating unincorporated molecules from the liposomes included chromatographing on a Sephacryl 300 column (Pharmacia) and equilibrating with PBS. In this method, the liposomes should be in the void volume and/or in the first few fractions. These fractions were used for further study. In yet a third method, hydrated liposome preparations were dialyzed in PBS using tubing with a 50,000 dalton relative molecular weight cutoff.

When the liposome preparations were centrifuged, reactivity toward samples with antiligand antibodies (i.e. antiphospholipid antibodies) were found in both the supernatant and the pellet of liposomes, indicating that liposomes or fragments thereof in which ligand (i.e. cardiolipin) was incorporated were present in both. The pellet was assumed to contain liposomes only and, therefore, pellet fractions were used in the examples, except where noted as supernatant.

Liposomes prepared as described in this example were stable (with respect to retention of reactivity with samples with antiphospholipid antibodies) under nitrogen at 4° C. for more than sixteen months when stored in microfuge or screw-capped plastic tubes.

EXAMPLE 2

Characterization of Liposome Reagent

A. Effect of Variations in the Molar Ratio of Haptenated Phospholipids to Ligand Phospholipids To examine the effect of varying the molar ratios of bt-DPPE to cardiolipin on incorporation of the biotinylated component, a forty-fold variation in the starting phospholipid ratio was studied. Cardiolipin-containing liposomes were prepared by mixing a solution of cardiolipin (5 mg/ml cardiolipin in ethanol, Sigma, St. Louis, Mo. USA) with a solution of bt-DPPE (1 or 5 mg/ml in a 2:1 mixture of chloroform to methanol, LC form of bt-DPPE, from Pierce, Rockford, Ill., Cat No. 22010). Liposome preparations were made having the following bt-DPPE:CL ratios: 1:100, 1:50, 1:25, 1:10, 1:5 and 1:2.5 by mixing a constant amount of cardiolipin (100 µg) with varying amounts of bt-DPPE from 0 µg to 40 µg. Ethanol was added to each preparation to a total volume of 200 µl, the preparations were vortexed and then dried onto tubes in films as described in Example 1. The lipid films were hydrated as described above and unincorporated molecules removed through centrifugation. The liposome-containing pellets were then resuspended in PBS to a concentration of 40 µg/ml of total phospholipids.

In order to determine whether varying the ratio of bt-DPPE to cardiolipin in the liposomes affected the ability of the liposome reagent to be bound by the solid phase (anti-biotin paramagnetic particles in this example), assays were performed using an avidin-alkaline phosphatase conjugate (avidin-ALP conjugate) bound to bt-DPPE incorporated into liposomes to the solid phase through the anti-biotin antibody-biotin interaction.

The assay components included the liposome reagent preparations having varying ratios of bt-DPPE and one preparation with cardiolipin only liposomes, anti-biotin paramagnetic particles, avidin-ALP conjugate in dilution buffer, wash buffer and a chemiluminescent substrate.

The paramagnetic particles used in these assays were obtained from Rhone Poulenc (Paris, France) and coated with goat anti-biotin antibodies as described below. The anti-biotin antibodies were polyclonal antibodies obtained by injecting a keyhole limpet hemocyanin (KLH)-biotin immunogen into a goat and then affinity purifying the desired antibodies using a biotinylated BSA column. The particles were washed in deionized water and 2-(N-morpholino)ethanesulfonic acid (MES) buffer and activated by incubating them for about 30 minutes with a solution of N-hydroxysulfosuccinimide (sulfo-NHS) and 1-ethyl-3-(3-dimethylaminopropyl)-carbodiimide hydrochloride (EDC). The activated particles were separated from unreacted components by applying a magnetic field and resuspended in MES buffer. Burro anti-goat antibodies were adsorbed onto the particles by incubating a mixture of particles and anti-goat antisera (obtained from Pel-Freez, Inc., Rogers, Ark., and affinity purified on goat IgG) at 100 µg/ml for about two hours.

The particles were then washed in a buffer (1M glycine, pH 6.0) followed by a series of washes, first with Tris buffer at pH 8, then glycine buffer at pH 2.5 and then Tris buffer at pH 8 again. The particles were then resuspended in a storage buffer (Tris buffer with 0.1% BSA, preservatives and salt). The particles with bound anti-goat antibodies were combined with goat anti-biotin antisera obtained as described above at a concentration of 15 µg/mg and incubated overnight at ambient temperature.

The avidin-ALP conjugate was obtained from CalBiochem/Behring Diagnostics (La Jolla, Calif., Cat. #189732) and diluted to 0.25 µg/ml in dilution buffer pH 7.7. The dilution buffer used in these examples, included 0.1M Tris, 0.1% BSA, 0.25 mg/ml mouse IgG, 1.0 mM $MgCl_2$, 0.1 mM $ZnCl_2$, 0.15M NaCl, 0.2% Tween 20, 0.1% ProClin (a preservative manufactured by Rohm and Haas), 0.1% $NaN_3$, and 7% (v/v) heat inactivated normal equine serum (NES).

The wash buffer used in these examples includes 20 mM Tris, 0.15M NaCl, 0.05% (active solids) FC100 (a fluoroalkyl sulfonate surfactant, sodium salt, ionic detergent, commercially available from 3M, St. Paul, Minn.), and 0.1% ProClin.

The chemiluminescent substrate used in these assays was LumiPhos® brand dioxetane chemiluminescent substrate (LumiPhos® 530 is commercially available from Lumigen, Inc, Detroit, Mich. USA), a composition that reacts with alkaline phosphatase to produce a detectable chemiluminescent signal.

In this experiment 25 µl of each liposome preparation (20 µg/ml) was mixed with 50 µl of 1 mg/ml anti-biotin paramagnetic particles and the volume of the reaction mixture brought to about 250 µl with wash buffer and the mixture incubated for about 30 minutes at 37° C. The bound liposome reagent was then separated from unbound reaction components through a series of three separation and wash steps where the reaction vessel containing the paramagnetic particles was placed in a magnetic field and the particles were attracted to the sides of the vessel (magnetic separation step), the solution aspirated from the vessel and then the particles were resuspended in wash buffer. After the third wash and aspiration step, the particles were resuspended in a solution containing 100 µl of the avidin-ALP conjugate and 250 µl of wash buffer. The mixture was incubated for about 30 minutes at 37° C. and then the unbound conjugate was separated from the conjugate bound to the particles by magnetic separation and washing as described above. The particles were then mixed with 250 µl of the LumiPhos® 530 substrate and incubated for about 5 minutes and the luminescence of the mixture was measured using a luminometer and expressed as Relative Luminometer Units (RLUs).

As reflected in Table 1, liposomes having molar ratios of haptenated phospholipid to ligand (cardiolipin in this example) ranging from 1:2.5 to 1:100 bt-DPPE:CL were able to bind to the solid phase in sufficient quantities to produce a detectable chemiluminescent signal greater than background, and the S/N ratio increased as more bt-DPPE was incorporated into the liposomes. In Table 1, S/N stands for the signal-to-noise ratio. S/N in these examples was determined by subtracting the RLU value obtained with the control preparation (cardiolipin-only liposomes, no biotin present) from the RLU value obtained with the liposome reagent preparation used in the assay and dividing the result by the control preparation value [(bt-DPPE:CL RLU value−control RLU value)/control RLU value]. In these assays, an S/N ratio greater than 5 is considered positive (P) or significantly greater than background, an S/N ratio of between 2 and 5 is considered indeterminate or borderline (B) and an S/N ratio of less than 2 is considered negative (N).

TABLE 1

Bt-DPPE Titration Response With Avidin-ALP Conjugate

| Liposome Composition | BtDPPE:CL ratio | MEAN RLUs | S/N |
| --- | --- | --- | --- |
| CL only | n/a | 24,156 | 0 |
| bt-DPPE:CL | 1:100 | 648,818 | 26 |
| bt-DPPE:CL | 1:50 | 1,393,385 | 57 |
| bt-DPPE:CL | 1:25 | 1,844,640 | 75 |
| bt-DPPE:CL | 1:10 | 2,810,540 | 115 |
| bt-DPPE:CL | 1:5 | 3,737,520 | 154 |
| bt-DPPE:CL | 1:2.5 | 4,404,780 | 181 |

B. Effect of Varying the Total Phospholipid Concentration During Hydration

The liposome reagents of the invention were further examined using a fixed amount of total phospholipid and a molar ratio of bt-DPPE to cardiolipin of 1:10 but using different resuspension volumes in order to determine whether the lipid concentration during hydration affected the efficiency of the binding of the liposome reagents to the solid phase. The liposome reagent preparations used in this example were prepared as described above but hydrated in varying amounts of PBS with 1% HSA (human serum albumin): 400 µl (20 µg/ml total phospholipid), 200 µl (40 µg/ml total phospholipid), 80 µl (100 µg/ml total phospholipid), or 40 µl (200 µg/ml total phospholipid), respectively. The cardiolipin-only control was hydrated in 200 μl PBS with 1% HSA to a concentration of 40 μg/ml. Each of the liposome reagent preparations was assayed as described above. As shown in Table 2, within the range of total phospholipid concentrations tested, the hydration volume was not critical for functionality of the liposome reagent in this assay.

TABLE 2

Effect of Varying Phospholipid Concentration on Liposome Reagent

| Liposome Phospholipid Concentration | BtDPPE: CL ratio | MEAN RLUs | S/N |
|---|---|---|---|
| CL only | n/a | 24,156 | 0 |
| bt-DPPE:CL, 20 μg/ml | 1:10 | 3,168,020 | 130 |
| bt-DPPE:CL, 40 μg/ml | 1:10 | 2,810,540 | 115 |
| bt-DPPE:CL, 100 μg/ml | 1:10 | 2,059,150 | 84 |
| bt-DPPE:CL, 200 μg/ml | 1:10 | 2,865,070 | 118 |

C. Effect of Variations in the Molar Ratio of Haptenated Phospholipids to Ligand Phospholipids on the Ability of Liposome Reagents on Recognition by Antiphospholipid Antibodies in a Test Sample In order to determine whether varying the ratio of bt-DPPE to cardiolipin in the liposomes affected the ability of the liposome reagent to react with antiphospholipid antibodies in a serum sample, assays were performed using liposome reagent preparations with varying ratios of bt-DPPE as well as one preparation with cardiolipin-only liposomes. The liposome preparations were combined with serum containing antiphospholipid antibodies (as determined using The Diastat Anti-Cardiolipin Kit from Shield Diagnostics Ltd., The Technology Park, Dundee DD1 1SW, UK and the Kallestad Anti-Cardiolipin Microplate EIA kit from Sanofi Diagnostics Pasteur, Inc., Chaska, Minn. 55318), anti-biotin paramagnetic particles as described above, alkaline-phosphatase labeled conjugate of monoclonal anti-human IgG (anti-human IgG-ALP, Fc specific, obtained from The Binding Site, San Diego, Calif.), diluted to 0.1 μg/ml in dilution buffer, wash buffer and the chemiluminescent substrate.

The assays were performed as described above with 2 μl equivalents of serum, 100 μl anti-biotin paramagnetic particles, and the liposome reagent preparation combined in the first step of the assay. Also, the anti-human IgG-ALP conjugate was used in place of the avidin-ALP conjugate used in the assays described above.

As shown in Table 3, liposomes having molar ratios of haptenated phospholipid to ligand (cardiolipin in this example) ranging from 1:2.5 to 1:100 bt-DPPE:CL were able to bind antiphospholipid antibodies in the serum sample in sufficient quantities to produce a detectable chemiluminescent signal greater than background. Further, little change in the S/N ratio was observed with the varying amounts of bt-DPPE used in the preparation of the liposomes indicating sufficient capture capacity at a 1:100 ratio.

TABLE 3

Bt-DPPE Titration with Serum and Anti-IgG-ALP Phosphatase

| Liposome Reagent Composition | BtDPPE: CL ratio | MEAN RLUs | S/N |
|---|---|---|---|
| CL only | n/a | 677,022 | 0 |
| bt-DPPE:CL | 1:100 | 8,651,140 | 12 |
| bt-DPPE:CL | 1:50 | 9,622,645 | 13 |
| bt-DPPE:CL | 1:25 | 8,853,780 | 12 |
| bt-DPPE:CL | 1:10 | 8,310,435 | 11 |
| bt-DPPE:CL | 1:5 | 8,600,020 | 12 |
| bt-DPPE:CL | 1:2.5 | 6,497,990 | 9 |

D. Effect of Variations In Total Phospholipid Concentration During Hydration on the Ability of Liposome Reagents to Bind to Antiphospholipid Antibodies The liposome reagents of the invention were further examined by using a fixed amount of total phospholipid and one molar ratio of bt-DPPE to cardiolipin of 1:10 but using different resuspension volumes to determine varying such volumes affect the usefulness of the liposome reagents in detecting antiphospholipid antibodies. The liposome reagent preparations used in this example were prepared as described above but hydrated in varying amounts of PBS with 1% HSA, 400 μl (20 μg/ml), 200 μl (40 μg/ml), 80 μl (100 μg/ml), and 40 μl (200 μg/ml), respectively. The cardiolipin only control was hydrated in 200 μl PBS with 1% HSA.

Each of the liposome reagent preparations was assayed as described above using 100 μl (2 μl equivalents) of diluted human serum sample and the anti-human IgG-ALP conjugate. As shown in Table 4, within the range of total phospholipid concentrations tested, the results indicated no significant change in recognition by antiphospholipid antibodies due to the starting phospholipid concentration.

TABLE 4

Effect of Varying Phospholipid Concentration on Liposome Reagent Recognition by Antiphospholipid Antibodies

| Liposome Phospholipid Concentration | BtDPPE: CL ratio | MEAN RLUs | S/N |
|---|---|---|---|
| CL only | n/a | 677,022 | 0 |
| bt-DPPE:CL, 20 μg/ml | 1:10 | 9,182,860 | 13 |
| bt-DPPE:CL, 40 μg/ml | 1:10 | 8,310,435 | 11 |
| bt-DPPE:CL, 100 μg/ml | 1:10 | 10,285,220 | 14 |
| bt-DPPE:CL, 200 μg/ml | 1:10 | 8,945,220 | 12 |

Those skilled in the art can readily optimize their assays using these methods for determining the effect of lipid ratios and concentration on the effectiveness of the test assay.

EXAMPLE 3

Effect of Increasing Ligand Concentration in Assay

Liposome reagent preparations were prepared essentially as in Example 1, see above. In this case, 300 μl of 5 mg/ml of ligand solution (cardiolipin solution (1.5 mg)) and 300 μl of 1 mg/ml bt-DPPE (300 μg) for a 5:1 ratio were dried onto tubes. A stock solution of each preparation was obtained by hydrating with a total volume of 1.8 ml PBS. Ligand concentrations of 0–1 µg/test were analyzed with a cardiolipin positive control serum in an automated analyzer as follows: 100 µl of liposome reagent preparation, 100 µl of diluted serum sample (serum sample was either serum known to contain antiphospholipid antibodies or normal human serum), 50 µl of 1 µg/ml paramagnetic particles and 100 µl of equine anti-human IgG-ALP conjugate (0.6 µg/ml in PBS with human serum albumin 1%) were added to a reaction vessel one after the other (simultaneously) incubated for thirty minutes and then washed three times as described above in Example 2. LumiPhos® brand 530 dioxetane chemiluminescent substrate (250 µl) was added, and the luminescence of the sample measured. As seen in Table 5, increased binding of the antiphospholipid antibodies in serum was observed as the ligand concentration was increased.

TABLE 5

Ligand Titration with Sera

| Ligand Concentration (µg/ml) | MEAN | S/N |
|---|---|---|
| 0 | 196,034 | 0 |
| 0.25 | 2,128,345 | 9.86 |
| 0.5 | 4,066,795 | 19.7 |
| 1.0 | 7,696,555 | 38.3 |
| 1.5 | 9,890,825 | 49.5 |
| 2.0 | 12,135,000 | 60.9 |
| 5.0 | 17,695,300 | 89.3 |
| 10.0 | 21,466,300 | 109 |

EXAMPLE 4

Preparation of Liposome Reagents with Ro and La and Assays to Detect Anti-Ro/La Antibodies in Samples In this case 20 µl of cardiolipin solution (100 µg), 20 µl of bt-DPPE (100 µg), and 160 µl of ethanol were dried onto tubes as described in Example 1. To make the mixed liposome reagent preparations, the films prepared as above were hydrated with a total volume of 500 µl 20 mM phosphate buffer, pH 7.2–7.4, with 150 mM NaCl containing from 10–100 µg of the antigen to be incorporated resulting in liposome preparations having approximate molar ratios of 670:1–67:1 of phospholipid:antigen. After vortexing, the preparations were shaken for an additional 30 minutes, washed two times using in a micro centrifuge at 13,000×g.

In this example the antigen preparations used in the hydration step were preparations containing 10, 50 and 100 µg of affinity purified La antigen (La SSB-3000 obtained from Immunovision, Little Rock Ark.), one preparation containing 55 µg of affinity purified Ro antigen (Ro SSA-3000, Immunovision, Little Rock, Ark.) and one preparation containing a mixture of 50 µg La and 50 µg Sm antigen (Immunovision, Little Rock, Ark.).

The resulting liposome preparations were tested in assays such as those described in Example 2, using samples known to have antibodies to the autoantigens (determined using commercially available microplate ELISA kits). One sample contained antibodies to cardiolipin and other samples contained antibodies to Ro/La, also a normal human sera sample was used as a control. Briefly, 25 µl of the liposome reagent was combined with 100 µl diluted sera sample, 75 µl wash buffer and 50 µl of the anti-biotin antibody coated paramagnetic particles and the mixture incubated for thirty minutes at 37° C. After a series of wash and separation steps, 100 µl of anti-human IgG-ALP conjugate and 250 µl of wash buffer were added to the reaction vessel containing particles. This mixture was incubated for thirty minutes at 37° C. and after a series of wash and separation steps substrate was added and signal detected as previously described.

Table 6 shows the results obtained with each of the liposome reagent preparations at various dilutions with one patient (a human serum sample containing antibodies to Ro and La), a patient serum sample containing anti-cardiolipin antibodies, a normal human serum sample (nhs) and a control with no serum added (blank or bl).

TABLE 6

Assays with Ro/La Liposome Reagents

| Liposome Preparation | Blank | | | Patient Sample Anti-Ro/La Antibody Sample | | | Anti-Cardiolipin Antibody Sample | | | 03621 Normal Human Serum Sample | | |
|---|---|---|---|---|---|---|---|---|---|---|---|---|
| Composition all CL:bt-DPPE 10:1 | MEAN RLUS | nhs S/N | bl S/N | MEAN RLUS | nhs S/N | bl S/N | MEAN RLUS | nhs S/N | bl S/N | MEAN RLUS | nhs S/N | bl S/N |
| La-10 ug diluted 1/5 | 35,749 | 0 | 0 | 97,792 | 1 | 2 | 677,476 | 10 | 18 | 59,593 | 0 | 1 |
| La-50 ug diluted 1/5 | 34,226 | 0 | 0 | 242,654 | 3 | 6 | 701,305 | 11 | 19 | 58,423 | 0 | 1 |
| La-100 ug diluted 1/5 | 41,322 | 0 | 0 | 795,682 | 13 | 18 | 1,185,370 | 21 | 28 | 54,992 | 0 | 0 |
| La50/Sm50 ug diluted 1/5 | 34,865 | 0 | 0 | 297,373 | 5 | 8 | 1,180,510 | 21 | 33 | 53,155 | 0 | 1 |
| La-10 ug diluted 1/20 | 46,642 | 0 | 0 | 93,621 | 0 | 1 | 308,566 | 3 | 6 | 82,229 | 0 | 1 |
| La-50 ug diluted 1/20 | 43,554 | 0 | 0 | 139,176 | 1 | 2 | 333,817 | 4 | 7 | 73,984 | 0 | 1 |
| La-100 ug diluted 1/20 | 37,049 | 0 | 0 | 286,056 | 4 | 7 | 520,286 | 8 | 13 | 60,034 | 0 | 1 |
| La50/Sm50 ug diluted 1/20 | 38,520 | 0 | 0 | 168,394 | 2 | 3 | 480,948 | 7 | 11 | 62,759 | 0 | 1 |
| Ro-55 ug diluted 1/5 | 30,799 | 0 | 0 | 12,414,850 | 271 | 402 | 1,601,795 | 34 | 51 | 45,620 | 0 | 0 |
| Ro-55 ug diluted 1/20 | 41,763 | 0 | 0 | 4,044,070 | 60 | 96 | 554,077 | 7 | 12 | 66,271 | 0 | 1 |
| La-10 supernatant | 41,763 | 0 | 0 | 347,742 | 9 | 7 | 1,666,415 | 45 | 39 | 36,357 | 0 | 0 |
| La-50 supernatant | 28,531 | 0 | 0 | 1,531,055 | 33 | 53 | 1,667,800 | 36 | 57 | 45,634 | 0 | 1 |
| La-100 supernatant | 35,595 | 0 | 0 | 2,385,550 | 43 | 66 | 1,301,915 | 23 | 36 | 53,698 | 0 | 1 |
| La50/Sm50 supernatant | 39,048 | 0 | 0 | 910,164 | 15 | 22 | 1,206,410 | 20 | 30 | 56,229 | 0 | 0 |

These results indicate that is possible to detect autoimmune antibodies such as anti-Ro/La antibodies using liposome reagents having Ro and/or La associated with the liposome membrane. Particularly good signal was obtained with the liposome reagents having the Ro antigen associated with the membrane. Further, the results indicate that increasing the amount of La antigen added during the hydration step resulted in increased binding of anti-La antibodies. Optimization of the amount of antigen associated with liposome reagents useful in an assay of this format could be performed by adding increasing amounts of antigen during the hydration step until no further increase in amount of autoantibody binding was observed.

In addition to testing the liposomes found in the pellets of the liposome preparations containing 100 µg cardiolipin, 100 µg biotinylated DPPE and 10, 50, or 100 µg La antigen or a mixture of 50 µg La and 50 µg Sm, the supernatants of these preparation were also tested to determine whether antigen was intercalated or associated with the presumably smaller liposomes that did not pellet during the centrifugation step. The results of these assays are also shown in Table 6, and are designated "supernatant." These results demonstrate that the Ro, La and Sm antigens were incorporated or stably associated with liposomes in the supernatant of the liposome reagents as well as with those liposomes forming the pellet.

EXAMPLE 5

Use of Haptenated Liposomal Ligand in a Microplate ELISA Format

Liposomes incorporating cardiolipin and bt-DPPE were prepared essentially as in Example 1. In this case, the haptenated liposome reagent was bound by the analyte that was captured by an anti-human antibody (which binds to the Fc portion of the analyte antibodies) immobilized on the well of a microplate. In this case, the analyte/liposome reagent complex was detected using a conjugate comprising a receptor for the hapten and an alkaline phophatase label. Microplates (Nunc, Denmark #4-41653) were washed with deionized water and then coated with goat anti-human antibody (goat anti-human, anti-IgG, anti-IgM, Jackson Laboratories, Cat #109005127) as described below: Antibody was diluted to 1 mg/ml in 0.05M glycine/0.1M NaCl, pH 3, and incubated for 15 minutes at room temperature. The pH was neutralized by diluting the antibody solution in a 50 fold excess of 0.1M potassium phosphate, pH 7.4, for a final concentration of antibody of 20 µg/ml. 100 µl of the neutralized antibody solution was added to each well of washed plates and incubated overnight at 4° C. Then the plates were washed three times with PBS to remove unbound antibody, then incubated with PBS/1% BSA (Fraction V, Sigma Chemicals) for 60 minutes at 37° C.

The plates were washed and 100 µl of patient sample (diluted 1:25 in PBS with 0.1% BSA) were added to appropriate wells and incubated for two hours at 37° C. A normal human serum control and an antiphospholipid antibody sera were included as negative and positive controls.

After about two hours of incubation, the plates were washed three times in PBS. The liposome reagent preparations were prepared as in Example 2 but with CL:bt-DPPE ratios of 5:1 to 20:1 and a CL control with no bt-DPPE. 100 µl of each of the liposome preparations (1:25 and 1:100 dilutions of the original stock 1 mg/ml liposome reagent preparation) and a negative control (with no ligand) were added to appropriate wells and incubated for 90 minutes at room temperature.

The plates were washed three times to remove excess liposome reagent and a streptavidin-alkaline phosphatase conjugate (Jackson #016050084, diluted 1/10,000 in PBS/0.1% BSA), was added and the plates incubated for 60 minutes at room temperature. Then the plates were washed and 100 µl of a p-nitrophenyl phosphate (PNPP) substrate was added. After a 30 minute incubation the reaction was stopped and the amount of signal generated measured spectrophotometrically at 405 nm.

The results indicated that the liposome reagent was captured by antiphospholipid antibodies in the test sample.

EXAMPLE 6

Liposomal Ligand with Label Associated With Membrane

In this example, liposome reagents were prepared having a phospholipid ligand incorporated into the liposome membrane, along with the haptenated phospholipid and a protein, in this case, a label compound, alkaline phosphatase.

Five different liposome preparations were made generally as described in Example 1. In the first dry down step of the method described in Example 1, 20 µl of the cardiolipin stock solution (5 mg/ml) was combined with no bt-DPPE and 180 µl of ethanol in tube 1. In tubes 2–5, 20 µl of the cardiolipin stock solution was combined with 5 µl of bt-DPPE stock solution (5 mg/ml) and 175 µl of ethanol. In the hydration step, an alkaline phosphatase solution, (Boehringer, West Germany, Cat. #556602), an alkaline phosphatase buffer (the same buffer used in the alkaline phosphatase solution about, but without the enzyme, 3M NaCl, 1 mM MgCl$_2$, 0.1 mM ZnCl$_2$, 30 mM triethanolamine, pH 7.6) and phosphate buffer (50 mM, pH 7.2) were added in varying amounts to tubes 1–5 having the phospholipid films dried thereon. 110 µl of ALP solution and 890 µl of phosphate buffer were added to tube 1. 110 µl of ALP buffer, and 890 µl of phosphate buffer were added to tube 2. 22 µl of ALP solution, 88 µl of ALP buffer, and 890 µl of phosphate buffer were added to tube 3. 55 µl of ALP solution, 55 µl of ALP buffer, and 890 µl of phosphate buffer were added to tube 4. 110 µl of ALP solution and 890 µl of phosphate buffer were added to tube 5.

The tubes were vortexed and incubated as described in Example 1. The tubes were then washed to remove unincorporated ALP. Then 1 ml PBS was added to each preparation, mixed, centrifuged in a microfuge and supernatant removed. This wash step was repeated two more times and then the liposomal pellet resuspended in 500 µl of PBS. In order to determine whether the alkaline phosphatase was incorporated/associated with the liposome reagents, 25 µl of each of the liposome preparations was mixed with 50 µl of anti-biotin paramagnetic particles and the volume of the reaction mixture brought to about 250 µl with wash buffer and the mixture incubated for about 30 minutes at 37° C. The bound liposome reagent was then separated from unbound reaction components through a series of separation and wash steps as described in Example 2. The particles were then mixed with 250 µl of the LumiPhos® 530 substrate and incubated for about 5 minutes and the luminescence of the mixture was measured using a luminometer and expressed as Relative Luminometer Units (RLUs). Generation of signal indicated association of the ALP into or with the liposome.

TABLE 8

| | Alkaline Phosphatase Associated with Liposomes | | | | | | | | |
|---|---|---|---|---|---|---|---|---|---|
| Liposome Reagent Preparation | Tube 1 No bt-DPPE CL/ALP 550 µg/ml ALP | | Tube 2 No ALP CL/bt-DPPE | | Tube 3 100:1 CL/ALP 110 µg/ml ALP | | Tube 4 50:1 CL/ALP 220 µg/ml ALP | | Tube 5 20:1 CL/ALP 550 µg/ml |
| Dilution | MEAN | S/N | MEAN | S/N | MEAN | S/N | MEAN | S/N | MEAN | S/N |
| 1/10 | 157,050 | 0 | 10,980 | −1 | 1,705,640 | 10 | 3,996,975 | 24 | 7,854,840 | 49 |
| 1/100 | 37,316 | 0 | 9,976 | −1 | 324,739 | 8 | 782,348 | 20 | 1,531,940 | 40 |
| 1/1000 | 10,175 | 0 | 9,261 | 0 | 45,834 | 4 | 97,220 | 9 | 213,132 | 20 |
| 1/10,000 | 9,441 | 0 | 9,439 | 0 | 12,442 | 0 | 15,931 | 1 | 18,797 | 1 |

As shown in Table 8 the results indicated that ALP was associated/intercalated into the liposome reagents and the liposome reagents were functional after rudimentary separation by microfuging to remove unincorporated ALP. The S/N ratio was still increasing at the highest concentration of ALP used in the liposome preparation step indicating that additional ALP could be added to increase the S/N ratio if desired. In this example, the S/N ratio was determined as follows: [(Mean Value obtained with Liposome Reagent-Mean Value obtained with Liposome Reagent of same dilution in Tube 1)/Mean Value of Tube 1].

While particular embodiments of the invention have been described in detail, it will be apparent to those skilled in the art that these embodiments are exemplary rather than limiting, and the true scope of the invention is that defined in the following claims.

What is claimed is:

1. A liposome reagent for use in an assay to detect analyte in a test sample containing an analyte comprising:
   a liposome;
   a ligand chosen to bind specifically to the analyte and associated with the liposome membrane; and
   a haptenated component associated with the liposome membrane, where the hapten is chosen to bind specifically to a receptor on a solid phase; and where the ligand and haptenated component remain associated with a portion of the liposome membrane to maintain a linkage between the solid phase and ligand.

2. The reagent of claim 1 wherein the ligand comprises a protein, polypeptide or peptide fragment.

3. The reagent of claim 2, wherein the ligand includes an antibody fragment capable of binding protein.

4. The reagent of claim 1 wherein the ligand is nucleic acid.

5. The reagent of claim 1 wherein the analyte is antibody present in a patient sample.

6. The reagent of claim 1, wherein the ligand is noncovalently associated with the liposome.

7. The reagent of claim 1, wherein the ligand is covalently associated with the liposome.

8. The reagent of claim 6, wherein the ligand is Ro.

9. The reagent of claim 6, wherein the ligand is La.

10. A method for determining the presence or amount of analyte in a test sample comprising the steps of:
    contacting a liposome reagent comprising a liposome, a ligand chosen to bind specifically with the analyte and associated with the liposome membrane, and a haptenated component associated with the membrane of the liposome and where the hapten is chosen to bind specifically to a receptor on a solid phase of the assay, with test sample and the solid phase having the receptor to the hapten immobilized thereon, simultaneously or sequentially for a time and under conditions sufficient for the analyte in the sample to bind to ligand in the liposome reagent and for the liposome reagent to bind to the receptor on the solid phase; and
    detecting the presence or amount of analyte bound to the solid phase.

11. The method of claim 10 further comprising determining the amount or presence of analyte by contacting the solid phase to which analyte in the test sample is bound with a predetermined amount of a labeled reagent that will specifically bind to the analyte and detecting the label.

12. The method of claim 10 wherein the label is selected from the group consisting of enzymes, pigments radioisotopes, stable free radicals, chemiluminescent compounds, bioluminescent compounds, fluorescent compounds, dyes and enzyme substrates.

13. The method of claim 12 wherein the label is an enzyme.

14. The method of claim 13 wherein the label is an enzyme selected from the group consisting of alkaline phosphatase and horseradish peroxidase.

15. The method of claim 10 wherein the solid phase is selected from the group consisting of microtiter plates, polystyrene beads, magnetic particles, nitrocellulose strips, membranes, latex microparticles, and particles prepared from hydrocarbon polymers including polystyrene and polypropylene, glass, metals and gels.

16. The method of claim 15 wherein the solid phase is a suspendable particle.

17. The method of claim 16 wherein the solid phase is a paramagnetic particle.

18. A method for determining the presence or amount of antibodies to an autoimmune determinant in a test sample comprising the steps of:
    contacting a liposome reagent comprising a liposome, a ligand chosen to bind specifically with the antibodies to the autoimmune determinant associated with the liposome membrane, and haptenated component associated with the bilayer of the liposome and where the hapten is chosen to bind specifically to a receptor on a solid phase of the assay, with test sample and the solid phase having the receptor to the hapten immobilized thereon, simultaneously or sequentially for a time and under conditions sufficient for the antibodies to the autoimmune determinant present in the sample to bind to the ligand in the liposome reagent and for the liposome reagent to bind to the receptor on the solid phase; and
    detecting the presence or amount of antibodies to the autoimmune determinant bound to the solid phase.

19. The method of claim 18 wherein the ligand is Ro.

20. The method of claim 18 wherein the ligand is La.

21. The method of claim 18 wherein the haptenated component is a haptenated phospholipid.

22. The method of claim 21 wherein the phospholipid that is haptenated is selected from the group consisting of cardiolipin, phosphatidylinositol, phosphatidylcholine, phosphatidylserine, phosphatidylethanolamine, sphingomyelin and phosphatidic acid.

23. The method of claim 21 wherein the haptenated phospholipid is haptenated dipalmitoylphosphatidyl ethanolamine.

24. A kit for use in an assay to determine the presence or amount of analyte present in a test sample comprising:
  a liposome reagent comprising a liposome, a ligand chosen to bind specifically to the analyte and associated with the liposome membrane; and a haptenated component associated with the liposome membrane, where the hapten is chosen to bind specifically to a receptor on a solid phase and where the liposome is prepared so that during the assay the ligand and haptenated component remain associated with a portion of the bilayer to maintain a linkage between the solid phase and ligand, the solid phase with receptor; and
  labeled detector for analyte.

25. A liposome reagent for use in an assay to detect antibodies in a test sample comprising:
  a liposome;
  a phospholipid ligand chosen to bind specifically to the antibodies and associated with the liposome membrane; and
  a haptenated component associated with the liposome membrane and where the hapten is chosen to bind specifically to a receptor on a solid phase used in the assay;
  and where the liposome is prepared so that during the assay the phospholipid ligand and haptenated component remain associated with a portion of the bilayer to maintain a linkage between the solid phase and phospholipid ligand.

26. A liposome reagent for use in an assay to detect analyte in a test sample comprising:
  a liposome;
  a ligand chosen to bind specifically to the analyte and associated with the liposome membrane;
  a haptenated component associated with the liposome membrane where the hapten is chosen to bind specifically to a receptor on a solid phase; and
  a label compound that is an element of a signal detection system associated with the liposome membrane.

27. The liposome reagent of claim 26 wherein the label compound is an enzyme.

28. The liposome reagent of claim 27 wherein the label compound is alkaline phosphatase.

29. A liposomal soluble support matrix for use in an assay to detect analyte in a test sample comprising;
  a first liposome reagent comprising a liposome having a ligand chosen to bind specifically to an analyte in a test sample, wherein the ligand is associated with the liposome membrane; and a haptenated component associated with the liposome membrane, wherein the hapten is selected to bind specifically to a receptor; and
  a second liposome reagent comprising a liposome having the receptor wherein during the assay the haptenated component on the first liposome reagent binds the receptor on the second liposome reagent to form the soluble support matrix.

30. The matrix of claim 29, wherein the ligand comprises a protein, polypeptide or peptide fragment.

31. The matrix of claim 29, wherein the ligand includes an antibody fragment capable of binding protein.

32. The matrix of claim 29, wherein the hapten portion of the haptenated component is biotin.

33. A liposomal soluble support matrix for use in an assay to detect analyte in a test sample comprising;
  a liposome reagent comprising a liposome, a ligand chosen to bind specifically to the analyte and associated with the liposome membrane, a haptenated component associated with the liposome membrane, where the hapten is chosen to bind specifically to a receptor; and
  wherein during the assay receptor is added to bind the haptenated component and form said solid soluble support matrix.

34. The matrix of claim 33, wherein the ligand comprises a protein, polypeptide or peptide fragment.

35. The matrix of claim 33, wherein the ligand includes an antibody fragment capable of binding protein.

36. The matrix of claim 33, wherein the hapten portion of the haptenated component is biotin.

37. The matrix of claim 36, wherein the receptor is neutravidin.

38. A method for determining the presence or amount of analyte in a test sample comprising the steps of:
  contacting a plurality of ligand-bearing liposome reagent with a test sample, a receptor and a receptor-bearing solid phase simultaneously or sequentially for a time and under conditions sufficient for analyte present in the sample to bind to the ligand in the liposome reagent, for the receptor to bind the liposome reagent to form a matrix and for the liposome reagent to bind to the receptor on the solid phase, said ligand-bearing liposome reagent comprising a liposome, a ligand chosen to bind specifically with analyte in a test sample associated with the liposome membrane, and haptenated component associated with the bilayer of the liposome where the hapten is chosen to bind specifically to the receptor and to the receptor bearing solid phase; and
  detecting the presence or amount of analyte bound to liposome reagent bound to the solid phase.

39. The method of claim 38, wherein the hapten of the liposome reagent is biotin.

40. The method of claim 39, wherein the receptor is selected from the group consisting of neutravidin, streptavidin, avidin and antibody capable of specifically binding to biotin.

41. A method for determining the presence or amount of antibodies to an allergen in a test sample comprising the steps of:
  contacting a liposome reagent comprising a liposome, a ligand chosen to bind specifically with the antibodies to the allergen and associated with the liposome membrane, and haptenated component associated with the bilayer of the liposome and where the hapten is chosen to bind specifically to receptor on a solid phase of the assay, with test sample and the solid phase having the receptor to the hapten immobilized thereon, simultaneously or sequentially for a time and under conditions sufficient for the antibodies to the allergen present in the sample to bind to the ligand in the liposome reagent and for the liposome reagent to bind to the receptor on the solid phase; and
  detecting the presence or amount of antibodies to the allergen bound to the solid phase.

42. The method of claim 41, wherein the ligand is an allergen.

43. A kit for use in an assay to determine the presence or amount of analyte present in a test sample comprising:

a plurality of ligand-bearing haptenated liposome reagent capable of binding to analyte present in a test sample;

a receptor capable of binding to the hapten on the haptenated liposome reagent;

a receptor-bearing solid phase; and labeled detector for analyte detection.

* * * * *